(12) United States Patent
Pfeiffer et al.

(10) Patent No.: US 10,216,011 B2
(45) Date of Patent: Feb. 26, 2019

(54) EYEWEAR MEASURING SYSTEMS, METHODS AND DEVICES

(71) Applicants: iCoat Company, LLC, Santa Fe Springs, CA (US); Wiley X, Inc., Livermore, CA (US)

(72) Inventors: Thomas Pfeiffer, Santa Fe Springs, CA (US); Michael Bumerts, Livermore, CA (US); Lawrence Wickline, Santa Fe Springs (CA); Imtiaz Hasan, Santa Fe Springs, CA (US); Timothy George Stephan, Huntington Beach, CA (US); Dan Freeman, Livermore, CA (US); Arman Bernardi, Glendale, CA (US)

(73) Assignees: iCoat Company, LLC, Santa Fe Springs, CA (US); Wiley X, Inc., Livermore, CA (US)

( * ) Notice: Subject to any disclaimer, the term of this patent is extended or adjusted under 35 U.S.C. 154(b) by 0 days.

(21) Appl. No.: 15/659,388

(22) Filed: Jul. 25, 2017

(65) Prior Publication Data
US 2018/0024385 A1    Jan. 25, 2018

Related U.S. Application Data

(60) Provisional application No. 62/366,542, filed on Jul. 25, 2016.

(51) Int. Cl.
| G02C 13/00 | (2006.01) |
| A61B 3/11 | (2006.01) |
| A61B 3/00 | (2006.01) |
| A61B 3/14 | (2006.01) |

(52) U.S. Cl.
CPC ............ *G02C 13/005* (2013.01); *A61B 3/111* (2013.01); *A61B 3/0025* (2013.01); *A61B 3/14* (2013.01)

(58) Field of Classification Search
CPC ..... G02C 13/005; G02C 13/003; A61B 3/111; A61B 3/0025; A61B 3/113
USPC ......................................................... 351/204
See application file for complete search history.

(56) References Cited

U.S. PATENT DOCUMENTS

| 4,309,085 | A | 1/1982 | Morrison |
| 5,528,321 | A | 6/1996 | Blum et al. |
| 9,291,834 | B2 * | 3/2016 | Silva ....................... A61B 3/111 |
| 2002/0171806 | A1 | 11/2002 | Baumgarten |

(Continued)

FOREIGN PATENT DOCUMENTS

GB    2444959 A    6/2008

OTHER PUBLICATIONS

"The "Vartek Prima" Progressive Lens", Techtran Polylenses Ltd., Retrieved from the Internet http://www.techtranindia.com/pdf/downloads/vartek-prima-dispensing.pdf on Dec. 16, 2015, 10 pgs.

(Continued)

*Primary Examiner* — Mohammed A Hasan
(74) *Attorney, Agent, or Firm* — KPPB LLP

(57) ABSTRACT

Systems, methods and devices for measuring eyewear characteristics are provided. The eyewear measurement systems and devices comprise a plurality of measurement standard frames, each having lenses marked with visible gridlines specifically configured to the measurement standard frame to allow for the direct measurement of a PD and SH/FH with respect to each eye of the wearer.

20 Claims, 4 Drawing Sheets

(56) References Cited

U.S. PATENT DOCUMENTS

| | | | |
|---|---|---|---|
| 2004/0004633 A1* | 1/2004 | Perry | G06Q 30/0603 |
| | | | 715/728 |
| 2014/0279179 A1 | 9/2014 | Balter | |
| 2015/0055085 A1* | 2/2015 | Fonte | G06Q 30/0621 |
| | | | 351/178 |

OTHER PUBLICATIONS

Cordova, "In Pursuit of Precision", Oct. 2007, Retrieved from the Internet http://www.ecpmag.com/ce/in-pursuit-of-precision.asp on Dec. 16, 2015, 6 pgs.

* cited by examiner

EYEWEAR MEASURING SYSTEMS, METHODS AND DEVICES

CROSS-REFERENCE TO RELATED APPLICATIONS

The current application claims priority to U.S. Provisional Application No. 62/366,542, filed Jul. 25, 2016, the disclosure of which is incorporated herein by reference.

FIELD OF THE INVENTION

Eyewear measuring systems, methods and devices, including systems, methods and devices for measuring pupillary distance and multifocal/fitting or segment height are provided.

BACKGROUND OF THE INVENTION

An eyeglass prescription is an order written by an eyewear prescriber, such as an optometrist or ophthalmologist, that specifies the value of all parameters the prescriber has deemed necessary to construct and/or dispense corrective lenses appropriate for a patient. If an examination indicates that corrective lenses are appropriate, the prescriber generally provides the patient with an eyewear prescription at the conclusion of the exam.

The parameters specified on spectacle prescriptions vary, but typically include the power to which each lens should be made in order to correct blurred vision due to refractive errors, including myopia, hyperopia, astigmatism, and presbyopia. It is typically determined using a phoropter and asking the patient which of two lenses is better, or by computer automated refractor, or through the technique of retinoscopy. A dispensing optician will take a prescription written by an optometrist or ophthalmologist and order and/or assemble the frames and lenses to then be dispensed and sold to the patient.

In addition to the correction parameters certain physical parameters must be measured to ensure the proper fit of the corrective optic to the wearer. Two key parameters are pupillary distance and segment height or fitting height. Pupillary Distance (PD) is the distance between pupil centers, usually expressed in millimeters. It is sometimes known as the Interpupillary Distance (IPD). It is written as two values if the prescription is for bifocals or progressive lenses—these are the pupillary distances for the distance and near fixation (essentially, the upper and lower part of the lenses). They differ due to pupillary convergence when looking at near objects. Additionally, an eyeglasses prescription may include a monocular pupillary distance ("monocular PD"), especially in situations of non-symmetrical faces. These measurements indicate, in millimeters, the distances from the center of each pupil to the center of the nose where the center of the frame bridge rests. PD measurements are essential for all spectacle dispensings, monocular PDs being essential in progressive lenses and for those with high prescription. Segment Height (SH), also known as Seg Height, in a multifocal lens, such as a progressive or bifocal lens, also referred to as Fitting Height (FH) in single vision lens, is the vertical measurement in millimeters from the bottom of the lens in a frame, to the center of pupil for a single vision or a progressive lens, or to the bottom of lower eyelid for a lined bifocal. The determined segment height/fitting height is specific to each frame and wearer.

SH/FH and PD values are typically measured by a skilled professional using a pupilometer and/or by using a ruler. The need to have professional optical staff make these key measurements limits the ability of retailers to expand into the area of prescription optical frames, such as for example, for prescription sunglasses. Accordingly, a need exists for a simplified eyewear measuring system.

BRIEF SUMMARY OF THE INVENTION

The application is directed to eyewear measuring systems, devices and methods.

Many embodiments are directed to an eyewear measurement system including:
  at least one measurement standard eyewear frame having one or more lenses;
  wherein the one or more lenses have a set of visible interconnecting gridlines having vertical and horizontal axes disposed thereon, the lenses and gridlines configured to be overlaid atop a user's pupils when worn by a user; and
  wherein the vertical and horizontal axes are separately labeled and configured to be indicative of at least pupillary distance and segment height such that each coordinate point on the grid provides a simultaneous measurement of both pupillary distance and segment height of a user's pupil in a single measurement.

In other embodiments the system includes a plurality of differentially sized standard eyewear frames.

In still other embodiments the gridlines are bounded by a visible perimeter box.

In yet other embodiments separate interconnecting gridlines are provided for each of the user's pupils.

In still yet other embodiments the grid has an overall shape selected from the group consisting of squares, rectangles, circles, and polygons.

In still yet other embodiments the horizontal axis provides one of either pupillary or interpupillary distance.

In still yet other embodiments the vertical axis provides the segment height.

In still yet other embodiments the coordinates on the gridline provide a direct measurement of both pupillary distance and segment height.

In still yet other embodiments the coordinates on the gridline are arbitrary and the measurement of both pupillary distance and segment height are provided by a separate lookup table.

In still yet other embodiments the grids are etched into the lenses.

In still yet other embodiments the grids are attached to the lenses by a transparent removable film.

Many other embodiments are directed to methods of measuring the position of a user's pupil including:
  providing a measurement standard eyewear frame having one or more lenses, wherein the one or more lenses have a set of visible interconnecting gridlines having vertical and horizontal axes disposed thereon, and wherein the vertical and horizontal axes are separately labeled and configured to be indicative of at least pupillary distance and segment height such that each coordinate point on the grid provides a simultaneous measurement of both pupillary distance and segment height of a user's pupil in a single measurement;
  positioning the measurement standard eyewear frame on the user's face such that the gridlines overlay atop the user's pupils;
  determining the coordinate of the gridlines centered on each of the user's pupils; and obtaining the pupillary distance and segment height of each of the user's pupils from the determined coordinates.

In other embodiments the method includes marking the position of the user's pupils on the lenses.

In still other embodiments the measurer is positioned at a distance of between 15 to 20 inches from the user.

In yet other embodiments the method includes looking up the coordinate in a separate lookup table.

In still yet other embodiments the method includes repeating the measurement at least twice for each pupil.

In still yet other embodiments the gridlines are bounded by a visible perimeter box.

In still yet other embodiments separate interconnecting gridlines are provided for each of the user's pupils.

In still yet other embodiments the horizontal axis provides one of either pupillary or interpupillary distance.

In still yet other embodiments the vertical axis provides the segment height.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

BRIEF DESCRIPTION OF THE DRAWINGS

The description will be more fully understood with reference to the following figures, which are presented as exemplary embodiments of the invention and should not be construed as a complete recitation of the scope of the invention, wherein.

DETAILED DESCRIPTION OF THE INVENTION

Turning now to the drawings, systems, methods and devices for measuring eyewear characteristics are described. In many embodiments, eyewear measurement systems and devices comprise a plurality of measurement standard frames, each having lenses marked with visible gridlines specifically configured to the measurement standard frame to allow for the direct measurement of a PD and SH/FH with respect to each eye of the wearer. In many such embodiments the lenses of the measurement standard frames are engraved with the visible gridlines. In various embodiments, the vertical and horizontal lines of the gridlines are each provided with a label, such as a unique numeric or alpha-numeric character. In some embodiments the lenses are designed of materials that allow for the marking of a point on the gridline by a suitable marking medium, such as, for example, an ink (indelible or erasable or waterproof) or other marking material. Other embodiments are directed to methods of performing eyewear measurements using the eyewear measurement systems and devices.

Figure 1:
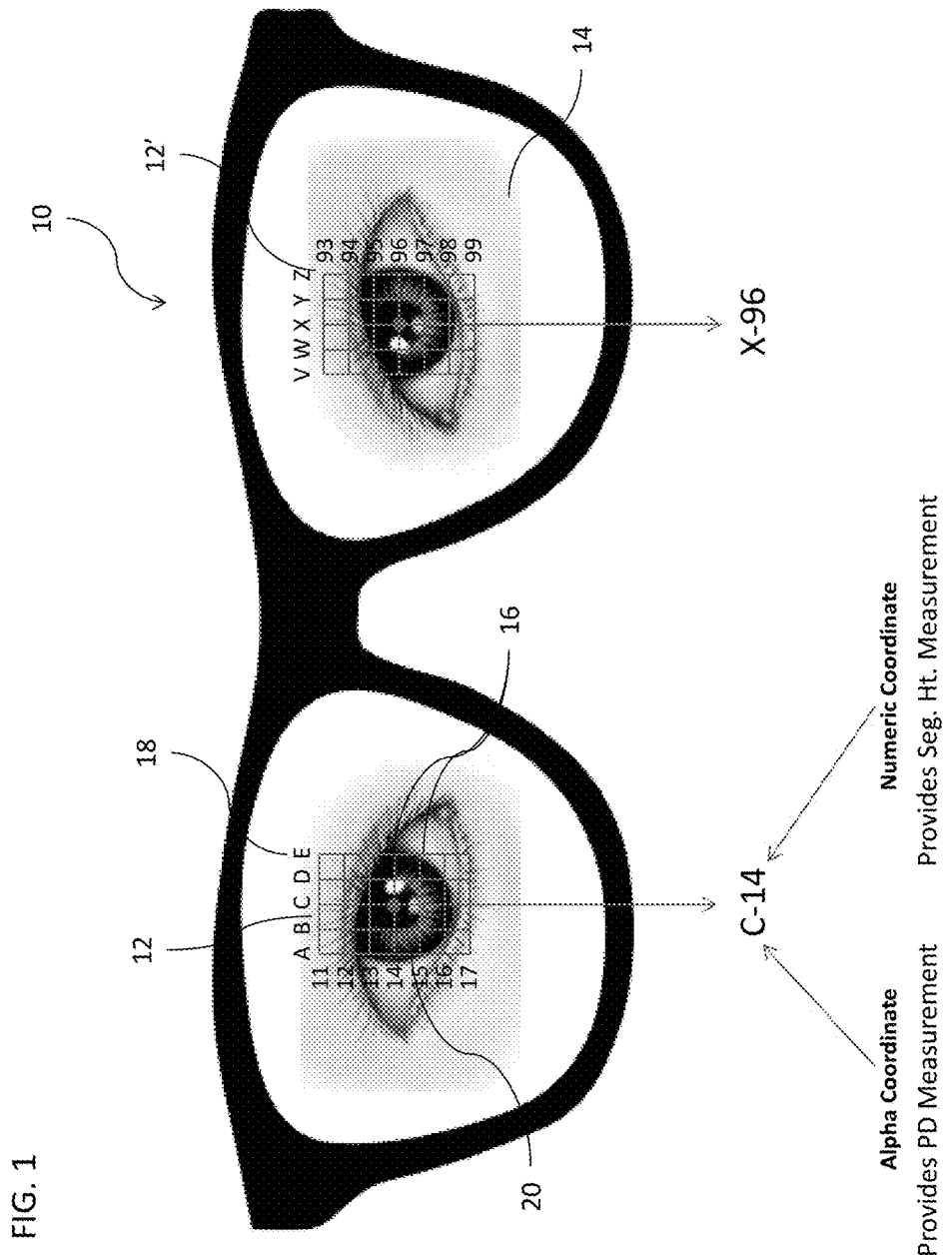
FIG. 1 provides a schematic of an eyewear measurement system incorporating an alpha-numeric grid in accordance with embodiments of the invention.

As shown in FIG. 1, in many embodiments an eyewear measurement device is provided comprising a standard measurement frame (10), which may be a specific frame design or a frame of a size that may be substituted as a generic version of the specific frame designs of interest. The standard measurement frame (10) is provided with a set of measurement grids (12 & 12') on each of the lenses (14) of the frame. The measurement grids (12 & 12') are each formed of a plurality of interconnecting gridlines (16) bounded by a surrounding perimeter box to provide a visual boundary to the grid. Although a rectangular grid is shown in the figures, it should be understood that grid having other shapes, including squares, circles and other polygons may be provided so long as a grid coordinate system can be defined in association with the horizontal and vertical gridlines of the grid. Regardless of the shape of the grid or the number of the gridlines, the gridlines (16) are each labeled (18) such that a unique coordinate may be determined and recorded for each lens via a single measurement.

In many embodiments the generic version of the frame design is configured such that the placement of the pupil relative to the gridline is conserved. This can be accomplished, for example, by ensuring that the position of the bridge when placed on the wearer's nose disposes the grid formed on the lenses centrally relative to the position of the wearer's pupils. In such embodiments the outer configuration of the lenses and frame are irrelevant provided that the bridge and gridline measurements of the generic frame overlap those of the specific frame being measured. For example that the height and width measurements to the center of the lens relative to the wearer's face are the same for the generic and specific frames. Using such generic frames it is possible to reduce the number of different frames needed to accomplish measurement for a wide array of different frame styles.

As shown in FIG. 1, the grids (12 & 12') are located on the lens such that they overlap the location of the wearer's pupil (20) when the frame (10) is properly positioned on the wearer's face. Although a grid (12) that is inscribed on only a central portion of each lens (14) that directly overlaps the pupil of the wearer's eye is shown in FIG. 1, it should be understood that the grid be formed to overlay atop a greater proportion of the lens (14), as shown schematically in FIG. 2. Any such size and position of grid may be contemplated in association with the standard measurement frames of the application so long as the grid at least overlaps the portion of each lens of the frame where the wearer's pupil will be located when the frames are worn by the wearer. In addition, the grid can be further customized per each specific frame so that it only shows the valid range for fitting that frame based on the lens selected, e.g., by providing a colored portion of the grid that must overlap the wearer's eyes to make a measurement. For example, an adult frame grid when worn by a child will likely not be positioned in a manner such that the central portion of the grid is disposed in front of the child's pupils thus indicating that the wearer should select another appropriate frame.

Figure 2:
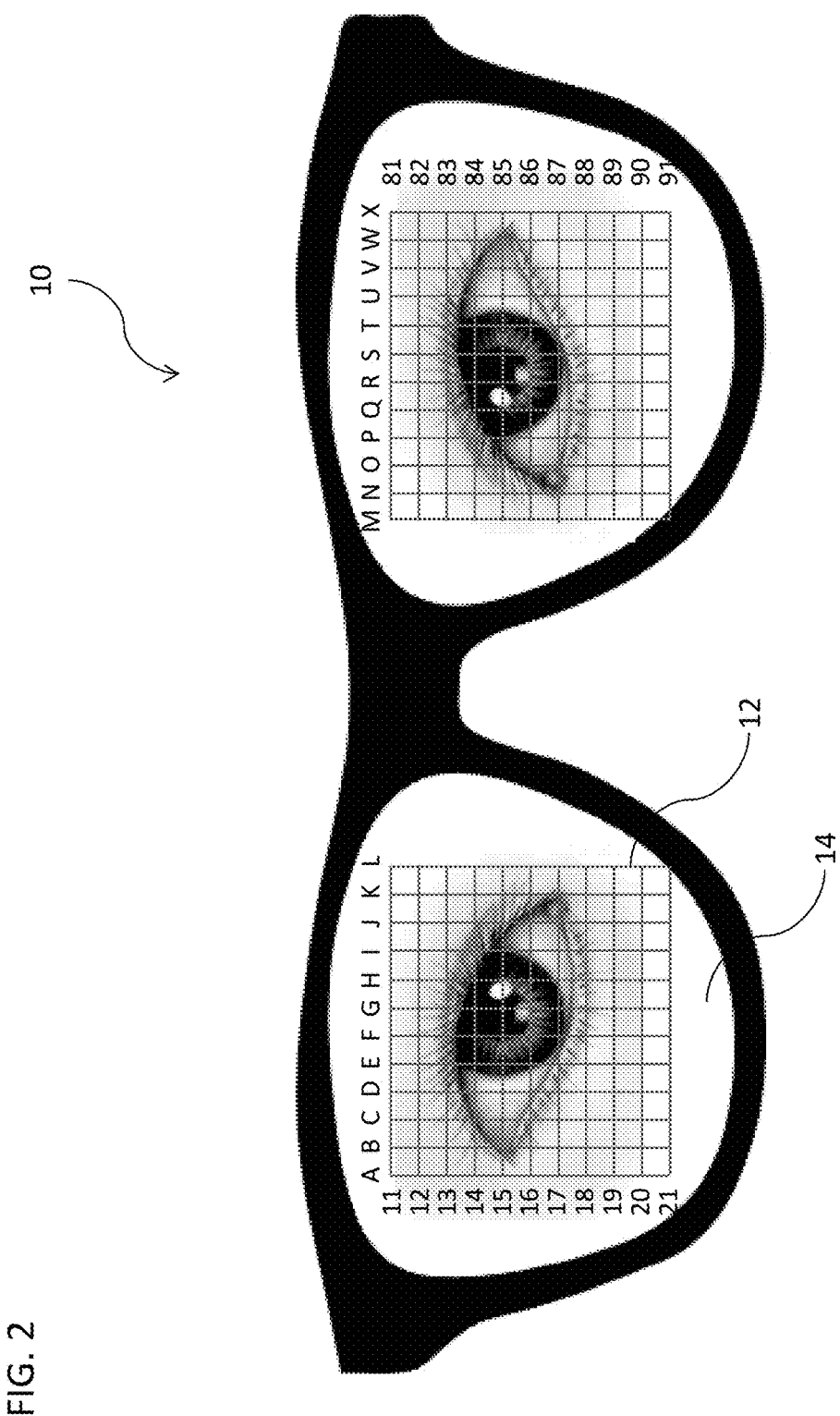
FIG. 2 provides a schematic of another embodiment of an eyewear measurement system incorporating an alpha-numeric grid in accordance with embodiments of the invention.
Figure 3:
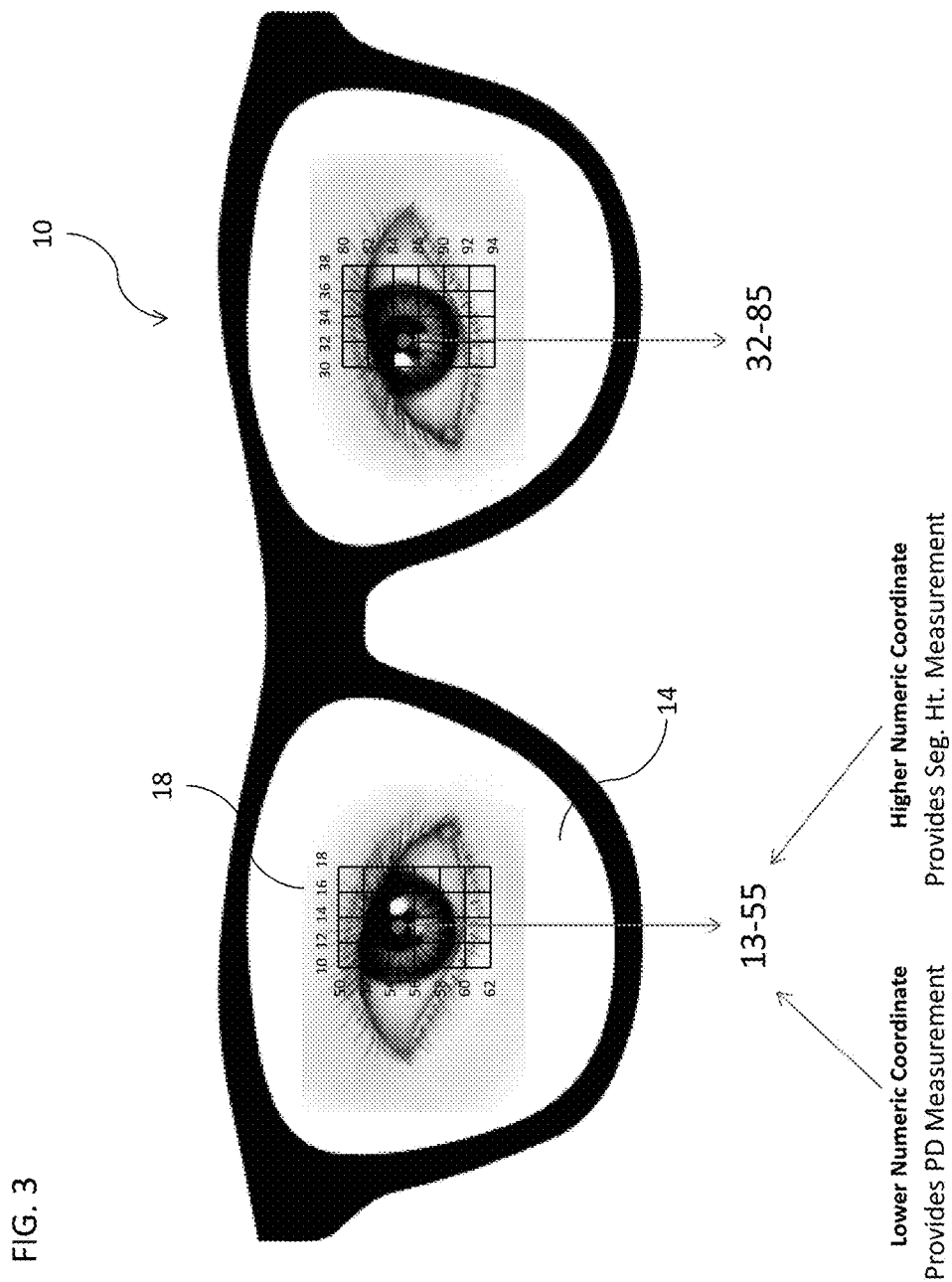
FIG. 3 provides a schematic of an eyewear measurement system incorporating a numeric grid in accordance with embodiments of the invention.

In addition, although the grids (12 & 12') of FIGS. 1 and 2 shown grid labels (18) where a unique alpha-numeric code is provided, it should be understood that the grid label may include any combination of markings capable of allowing a user to determine and record a unique coordinate identifier. For example, the labels (18) may be purely numeric, as shown in FIG. 3, or may include symbols, colors or other identifying features. Regardless of the specific labels used for the grids, it should be understood that the horizontal axis of the grid will provide the pupillary or interpupillary distance (PD), while the vertical axis of the grid will provide the segment height (SH)/Fitting Height (FH). A description of the method for determining both PD and SH/FH will be provided in greater detail below. Although the grid labels (18) could be arbitrary such that a corresponding look-up chart would be consulted during measurement to determine the PD and SH/FH of the specific frame, in other embodiments the labels provide a direct measurement of the distance of the coordinate space from the center of the frame (e.g., the PD measurement), and/or the distance from the bottom of the frame (e.g., the SH/FH measurement). Regardless of the specific grid or gridlines used, the grid system in accordance with embodiments allows for the determination of both PD and SH/FH in a single measurement, reducing the chance for error.

In many embodiments, the lens may be formed of a glass, plastic or other transparent material suitable for use in forming a lens capable of allowing the wearer's pupil to be seen therethrough. In various embodiments, the grid disposed on the lenses may be marked or etched permanently into the lens itself. Alternatively, the grid lines may be applied via decal, sticker, paint, ink, etc. In addition, the lens of the standard measurement frames may be coated such as by a vinyl, acrylic or polypropylene material, such that the proper grid coordinate may be directly and removably marked. Alternatively, the system may include a special pen or pencil that enables the removable marking of the standard measurement frame, such as a xylene and/or toluene free marker or a grease pencil, for example. Finally, in many other embodiments where engraved gridlines, such as by marking or etching accomplished by mechanical, electro-chemical, or other means, are utilized the lenses of the standard measurement frames may be treated with a coating such that the gridlines are clearly visible, such as via a translucent paint or pigment.

Although only a single standard measurement frame device is shown in the schematics provided in FIGS. 1 to 3, it will be understood that any number of standard measurement frames may be provided with the eyewear measurement system such that all frame designs offered by any particular retail establishment may have a corresponding measurement frame suitable for providing measurements for said frame. In turn, each standard measurement frame would require a separate look-up chart corresponding to that frame and grid system. Embodiments of the eyewear measurement system incorporate these various measurement frames and look-up charts.

Figure 4:
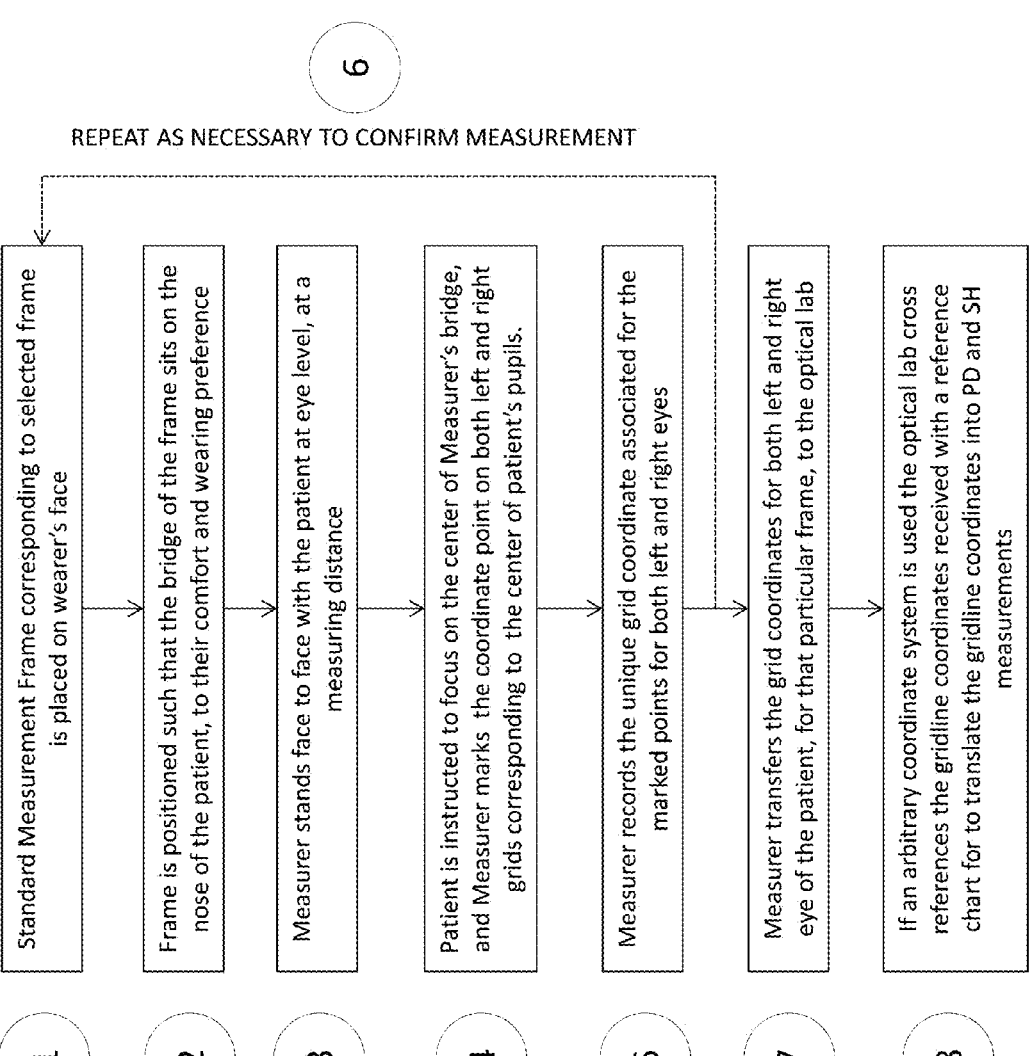
FIG. 4 provides a flowchart of a method for eyewear measurement in accordance with embodiments of the invention.

Turning now to methods of measuring the eye, FIG. 4 provides a flowchart of such methods in accordance with embodiments. As shown in accordance with many embodiments the method generally comprises:

Step 1: Measurer should have the patient place a standard measurement frame corresponding to the selected frame on to their face.

Step 2: The standard measurement frame should be placed such that the bridge of the frame sits on the nose of the patient, to their comfort and wearing preference.

Step 3: Measurer should then stand face to face with the patient at eye level at a range suitable to allow them to mark the position of the wearer's pupil on the relevant grid. In some embodiments the distance may be, for example, at approximately 15 to 20 inches from the patient.

Step 4: Measurer has the patient focus on the center of measurer's bridge, and then notes the location of the center of the patient's pupils on the gridline coordinates imprinted on the lens of the standard measurement frame. In some embodiments the measurer may use a suitable erasable marker, such as, for example, a waterproof marker, to place a mark on the grid.

Step 5: Measurer then has the patient remove the standard measurement frame and records the corresponding coordinate numbers from the gridlines for both left and right eyes.

Step 6: Optionally the measurer may repeat the measurement steps 1 to 5. In such embodiments the measurer has the patient place the eyewear on their face again and the measurer then checks the position of the patient's center of the pupils on the gridline coordinates to confirm the alpha-coordinates.

Step 7: After a final set of markings has been determined and recorded the measurer transfers the gridline coordinates for both left and right eye of the patient, for that particular frame, to the manufacturer, such as an optical lab. In embodiments where marks are made directly on the standard measurement frame, the measurer then cleans off the markings on the lens using an appropriate cleanser (e.g., cleaning swabs), so that the frame can be used again on another patient.

Step 8: The optical lab then cross references the gridline coordinates received from the retail location with the reference chart for that particular standard frame, and translates the gridline coordinates into actual PD and SH/FH measurements.

The current eyewear measurement devices, systems and methods allow for the measurement of PD and SH/FH for a particular frame on a particular patient, and provides for accurate and simple measurement using the gridline coordinate system described. Unlike PD rulers, pupilometers and application based tablet systems, which either only measure one of these values, or require sophisticate operators, the current eyewear measurement systems, devices and methods allow for such measurements by untrained personnel. Moreover, the system, methods and devices in accordance with embodiments allow for the PD and SH/FH of each eye to be measured independent of the other eye, providing accurate measurements for each eye. This is particularly helpful for non-symmetrical faces. Because the PD and SH/FH measurements are specific to each frame, accommodating every age group, they are also more accurate. Moreover, although the operation of the systems, methods and devices is relatively straight-forward they provide a system that can generally measure any PD and any SH/FH (e.g., the measurable PD for adults is in some embodiments approx. 55 to 73 mm and for children is in some embodiments from 41 to 55 mm, while the measurable SH/FH for multifocal optics in some embodiments ranges 10 to 29 mm, depending on the frame.)

Doctrine of Equivalents

As can be inferred from the above discussion, the above-mentioned concepts can be implemented in a variety of arrangements in accordance with embodiments of the invention. Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. An eyewear measurement system comprising
   at least one measurement standard eyewear frame having one or more lenses, and being configured to be worn by a user;
   wherein the one or more lenses have one or more visible grids having vertical and horizontal axes disposed thereon each of the one or more grids being comprised of a plurality of fixed visible horizontal and vertical gridlines, the gridlines being arranged such that each of the plurality of horizontal gridlines intersect at unique locations with each of the plurality of horizontal gridlines to define a plurality of fixed coordinate points, the lenses and grids being configured to overlay a portion of a wearer's field of view when worn by the wearer; and
   wherein the vertical and horizontal axes are separately labeled and configured to be indicative of at least pupillary distance and segment height such that each coordinate point on the grid provides a simultaneous measurement of both pupillary distance and segment height of a user's pupil in a single measurement.

2. The system of claim 1, comprising a plurality of differentially sized standard eyewear frames.

3. The system of claim 1, wherein the gridlines are bounded by a visible perimeter box.

4. The system of claim 1, wherein separate intersecting gridlines are provided for each of the user's pupils.

5. The system of claim 1, wherein the grid has an overall shape selected from the group consisting of squares, rectangles, circles, and polygons.

6. The system of claim 1, wherein the horizontal axis provides one of either pupillary or interpupillary distance.

7. The system of claim 1, wherein the vertical axis provides the segment height.

8. The system of claim 1, wherein the coordinate points provide a direct measurement of both pupillary distance and segment height.

9. The system of claim 1, wherein the coordinate points on the gridline are arbitrary and the measurement of both pupillary distance and segment height are provided by a separate lookup table.

10. The system of claim 1, wherein the grids are etched into the lenses.

11. The system of claim 1, wherein the grids are attached to the lenses by a transparent removable film.

12. A method of measuring the position of a user's pupil comprising:
    providing a measurement standard eyewear frame having one or more lenses, wherein the one or more lenses have a set of visible intersecting gridlines having vertical and horizontal axes, each intersection defining a coordinate point, and wherein the vertical and horizontal axes are separately labeled and configured to be indicative of at least pupillary distance and segment height such that each coordinate point on the grid provides a simultaneous measurement of both pupillary distance and segment height of a user's pupil in a single measurement;
    positioning the measurement standard eyewear frame on the user's face such that the gridlines overlay atop the user's pupils;
    determining a coordinate point of the gridlines centered on each of the user's pupils; and
    obtaining the pupillary distance and segment height of each of the user's pupils from the determined coordinates.

13. The method of claim 12, further comprising marking the position of the user's pupils on the lenses.

14. The method of claim 12, wherein the measurer is positioned at a distance of between 15 to 20 inches from the user.

15. The method of claim 12, further comprising looking up the coordinate in a separate lookup table.

16. The method of claim 12, further comprising repeating the measurement at least twice for each pupil.

17. The method of claim 12, wherein the gridlines are bounded by a visible perimeter box.

18. The method of claim 12, wherein separate interconnecting gridlines are provided for each of the user's pupils.

19. The method of claim 12, wherein the horizontal axis provides one of either pupillary or interpupillary distance.

20. The method of claim 12, wherein the vertical axis provides the segment height.

* * * * *